(12) United States Patent
Oroskar

(10) Patent No.: US 9,546,125 B2
(45) Date of Patent: Jan. 17, 2017

(54) CONTINUOUS PROCESS FOR EXTRACTION OF UNSATURATED TRIGLYCERIDES FROM FISH OIL

(71) Applicant: Orochem Technologies, Inc., Naperville, IL (US)

(72) Inventor: Anil R. Oroskar, Oak Brook, IL (US)

(73) Assignee: OROCHEM Technologies, Inc., Naperville, IL (US)

( * ) Notice: Subject to any disclaimer, the term of this patent is extended or adjusted under 35 U.S.C. 154(b) by 80 days.

(21) Appl. No.: 14/619,443

(22) Filed: Feb. 11, 2015

(65) Prior Publication Data
US 2016/0229785 A1 Aug. 11, 2016

(51) Int. Cl.
| | |
|---|---|
| *C10L 1/00* | (2006.01) |
| *C07C 51/47* | (2006.01) |
| *B01D 15/18* | (2006.01) |
| *B01D 15/30* | (2006.01) |
| *C10L 1/02* | (2006.01) |

(52) U.S. Cl.
CPC ............. *C07C 51/47* (2013.01); *B01D 15/185* (2013.01); *B01D 15/305* (2013.01); *C10L 1/026* (2013.01); *C10L 2200/0476* (2013.01); *C10L 2270/026* (2013.01); *C10L 2290/544* (2013.01); *C10L 2290/547* (2013.01)

(58) Field of Classification Search
CPC ............. C10L 1/026; C10L 2200/0476; C10L 2270/026; C10L 2290/544; C10L 2290/547; B01D 15/185; B01D 15/305; C07C 51/47
See application file for complete search history.

(56) References Cited

U.S. PATENT DOCUMENTS

| | | | | |
|---|---|---|---|---|
| 2,985,589 | A | | 5/1961 | Broughton |
| 4,792,418 | A | * | 12/1988 | Rubin .................... C09F 5/10 435/134 |
| 5,719,302 | A | | 2/1998 | Perrut |
| 7,491,522 | B2 | | 2/2009 | Haraldsson |
| 7,709,668 | B2 | | 5/2010 | Catchpole |
| 8,663,725 | B2 | * | 3/2014 | Ortega .................... A23J 1/04 426/417 |
| 8,802,880 | B1 | | 8/2014 | Adam |
| 9,163,198 | B2 | * | 10/2015 | Oroskar .................. C11C 3/003 |
| 9,234,157 | B2 | * | 1/2016 | Kelliher ............... B01D 15/185 |
| 9,260,677 | B2 | * | 2/2016 | Kelliher ............... B01D 15/185 |
| 9,315,762 | B2 | * | 4/2016 | Kelliher ............... B01D 15/185 |
| 9,321,715 | B2 | * | 4/2016 | Kelliher ............... B01D 15/185 |

OTHER PUBLICATIONS

Lembke, Peter, Concentration Omega-3 Oils—Supercritical Fluid Technology versus Molecular Distillation, Bioseutica USA, pp. 6-8, 2011.*

* cited by examiner

*Primary Examiner* — Cephia D Toomer
(74) *Attorney, Agent, or Firm* — Richard P. Silverman & Assoc., LLC

(57) ABSTRACT

Disclosed is a process for the direct extraction of an omega-3 fatty acid enriched triglyceride product comprising unsaturated triglycerides with a fatty acid strand of docosahexaenoic acid (DHA) or eicosapentaenoic acid (EPA) from a crude fish oil comprising unsaturated triglycerides and saturated triglycerides having strands comprising fatty acids of at least one stearic acid, palmitic and oleic acid. Each triglyceride in the crude fish oil can be characterized by a Partition Number (PN) according to the formula:

$$PN = TC - 2DB$$

wherein TC is a total number of carbon atoms in the fatty acid strand, and DB is the number of double bonds in the fatty acid strand. Crude fish oil diluted in non-polar solvent directly passed to an SMB zone, comprising a normal phase separation with a hydrophilic stationary phase agent and a non-polar/organic polar mobile phase desorbent to provide an omega-3 fatty acid enriched triglyceride product.

10 Claims, 5 Drawing Sheets

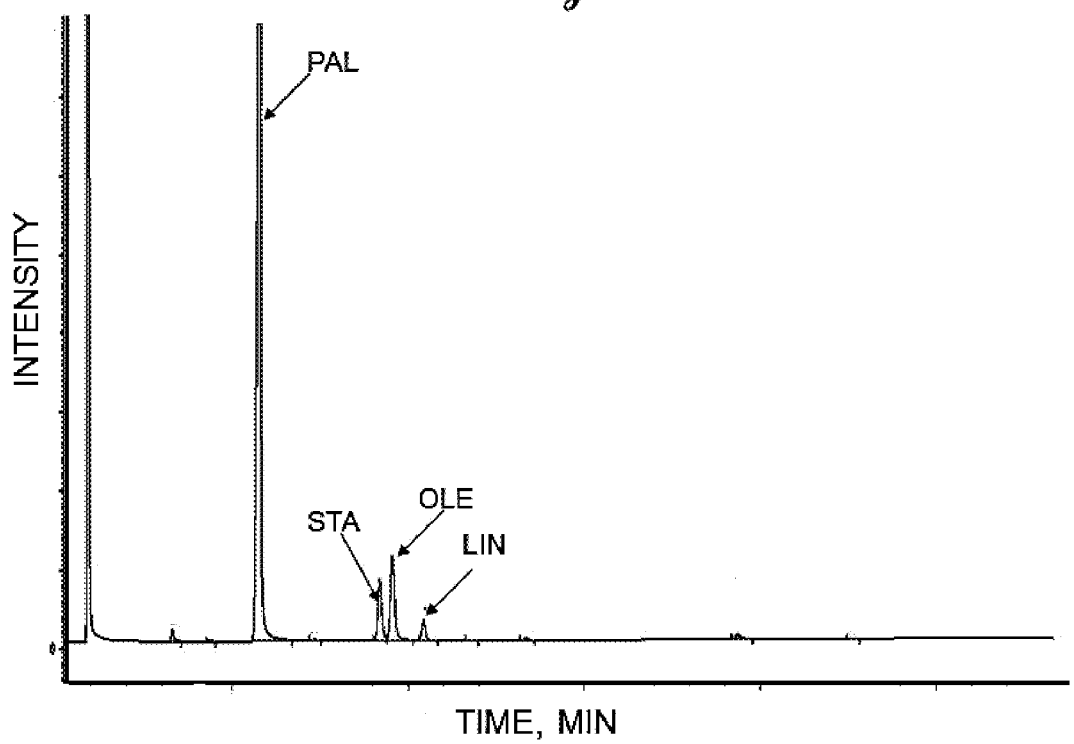

CONTINUOUS PROCESS FOR EXTRACTION OF UNSATURATED TRIGLYCERIDES FROM FISH OIL

FIELD OF THE INVENTION

The invention relates to a method for extracting unsaturated triglycerides having fatty acid strands of DHA (docosahexaenoic acid) from a crude fish oil feedstock in a continuous direct separation process which does not require the conversion of the triglycerides to ester form. More particularly, the invention provides for direct extraction of an omega-3 fatty acid enriched triglyceride product comprising DHA (docosahexaenoic acid) Triglycerides directly from crude fish oil feedstock using chromatographic technique of simulated moving bed continuous chromatography without the need for chemical or enzymatic pretreatment to convert the triglycerides to esters. Purified DHA (docosahexaenoic acid) Triglycerides may provide human health benefits. Intake of a recommended amount of DHA (docosahexaenoic acid) Triglycerides (in the form as it occurs in nature) has been shown to provide significant advantages in developing neural growth in children over DHA compositions which has first been converted to esters and then purified.

BACKGROUND

The principle components of crude fish oil are triglycerides, which can represent over 90 percent of the total composition of crude fish oil. The balance consists of partial glycerides; that is, mono- or diglycerides, free fatty acids, phospholipids and a group of chemicals known as the unsaponifiable fraction. Crude fish oils are very similar to one another in their physical nature. They are considered as liquid oils; but, in fact, they contain sufficient triglycerides of intermediate melting point for the oils to be partially solid at 20° C. The triglycerides usually occur in various combinations of less desirable fatty acids in between the more desirable DHA.

Fish oil is oil derived from the tissues of oily fish. Fish oils contain the omega-3 fatty acids eicosapentaenoic acid (EPA), and docosahexaenoic acid (DHA) along with other unsaturated triglyceride species including: docosapentanoic acid (DPA), stearadonic acid (SDA), alpha linolenic acid (ALA), gamma linolenic acid (GLA), linoleic acid (LIN) and oleic acid (OLE) and saturated triglycerides including stearic acid (STA) and palmitic acid (PAL). DHA and EPA are poly unsaturated omega-3 fatty acids. Omega-3 fatty acids (also called ω-3 fatty acids) are polyunsaturated fatty acids (PUFAs) with a double bond (C═C) at the third carbon atom from the end of the carbon chain. The fatty acids have two ends, the carboxylic acid (—COOH) end, which is considered the beginning of the chain, thus "alpha", and the methyl (CH$_3$) end, which is considered the "tail" of the chain, thus "omega." The nomenclature of the fatty acid is taken from the location of the first double bond, counted from the methyl end, that is, the omega (ω-). The three types of omega-3 fatty acids involved in human physiology are ALA (found in plant oils), EPA, and DHA (both commonly found in marine oils).

In nature the fatty acids combine as triplets with a glycerol back bone forming triglycerides (oil). The structures of EPA and DHA are shown hereinbelow:

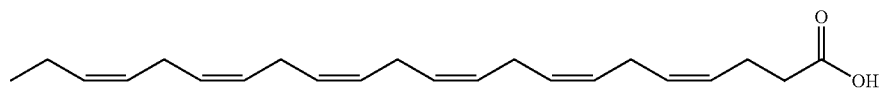

Docosahexaenoic Acid (DHA) (22:6 n-3)

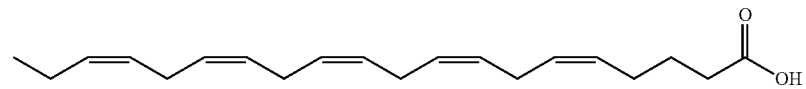

Eicosapentaenoic Acid (EPA) (20:5 n-3)

Omega-3 fatty acids are polyunsaturated fatty acids that are essential nutrients for health. Humans need omega-3 fatty acids for numerous normal body functions, such as controlling blood clotting and building cell membranes in the brain. Because human bodies cannot make omega-3 fatty acids, these omega-3 fatty acids must be obtained from food. Omega-3 fatty acids are also associated with many human health benefits, including protection against heart disease and possibly stroke. Recent studies are identifying potential benefits for a wide range of conditions including cancer, inflammatory bowel disease, and other autoimmune diseases such as lupus and rheumatoid arthritis. Triglycerides of DHA in naturally occurring form with a purity of greater than or equal to 40 weight percent have recently been shown to stimulate the neural growth in infants.

The major source of DHA and EPA is from marine oils, or fish oil derived from oily fish tissues and is in triglyceride form. Separation of unsaturated fats and fat derivatives from saturated fats and fat derivatives is difficult because the unsaturated components are susceptible to thermal and oxidative degradation and because their physical properties do not differ from those of the saturated components. The concentration of the unsaturated components in the form of parent triglycerides is more difficult, because the fatty acids are randomly arranged on the glycerol backbone of the triglyceride. Therefore the parent oil is usually converted into free fatty acids (FFA) or fatty acid ethyl esters (FAEE) before separation into polyunsaturated and saturated fractions is carried out.

Typically, crude fish oil is esterified at conventional esterification temperatures above about 60° C. The resulting conventionally esterified effluent is water washed and passed to a molecular distillation process for the separation of lower carbon number esters and to enrich the concentration of the Omega-3 ester components. The molecular distillation is typically carried out at a molecular distillation temperature in excess of about 200° C. at very low pressures of about 1 to about 10 mBar (0.1 to 1 kPa). This heating during the molecular distillation results in the breakdown of the EPA and causes isomers of EPA to form. The lower carbon number fatty acid esters and the isomers of EPA act as impurities in the subsequent purification steps to obtain a high purity EPA and DHA content products.

U.S. Pat. No. 7,491,522 to Haraldsson, for example, discloses a process for the lipase-catalyzed esterification of fish oil or marine oil. In Haraldsson, compositions which contain EPA and DHA as free acids or hexyl esters are esterified with ethanol in the presence of a lipase catalyst under essentially organic solvent-free conditions and separated by distillation. The process, the reaction is conducted at 40° C. under vacuum to remove co-produced water. At such conditions, at least a portion of the EPA is lost to isomerization into less valuable components.

The use of urea complexes to separate saturated and monounsaturated fatty acids from polyunsaturated fatty acids has been known since the 1950's. The separation procedure is typically performed by dissolving a mixture of FFA (or fatty acid derivatives) in a hot aqueous alcohol solution that contains the appropriate amount of urea. When the solution is cooled, the urea preferentially forms solid complexes with saturated fatty acids and these are removed by filtration. The aqueous alcohol filtrate solution, which is enriched in unsaturated fatty acids, also contains urea. Therefore the fatty acids are recovered from the filtrate by solvent extraction with a non-polar organic solvent, such as hexane or isooctane, in which the urea is insoluble. U.S. Pat. No. 7,709,668 discloses a process for extracting lipophilic compounds from urea-containing solutions comprising using a near-critical fluid to produce a urea containing precipitate and a near-critical fluid phase containing the lipophilic compound; separating the near-critical fluid phase from the urea containing precipitate; and reducing the pressure of the near-critical fluid phase to recover the lipophilic compound.

U.S. Pat. No. 5,719,302 discloses a process for recovering at least one of purified polyunsaturated fatty acids and polyunsaturated fatty acid mixtures using simulated continuous countercurrent moving bed chromatography which comprises a first step of either a stationary bed chromatography or multi-stage countercurrent column fraction followed by the step of simulated continuous countercurrent moving bed chromatography in which the solvent is at supercritical pressure to recover the purified polyunsaturated fatty acid or mixture thereof. The simulated continuous countercurrent moving bed chromatography process employs a stationary phase as a reverse phase bonded silica gel with alkanes of C8 or C18, especially C18 bonded silica gel and an eluent chosen from the group consisting of short chain alcohols, ethers, esters or ketones or mixtures thereof, or mixtures with water.

Heating fatty acids either in the transesterification of triglycerides to fatty acid esters, or in the subsequent separation of the desired fatty acid derivative from a solvent or co-solvent has been shown to isomerize the EPA molecules and reduce the overall recovery of these valuable components.

Previous methods for extraction of EPA, DHA and other useful polyunsaturated fatty acids from their triglycerides, have not been satisfactory for the purification of DHA triglycerides from crude fish oils, or for the production of purified fatty acids. The term "purity" is used here to mean not only in the sense of being separated from all other fatty acids of different chain lengths and different number and placement of unsaturations, but also purity of the particular cis-trans structure. Prior art methods not only did not yield sufficient purity, but in many cases also required such extreme physical and chemical conditions as to cause some degree of degradation of the fatty acids, formation of peroxides, and/or conversion of at least some of the cis-bonds to the less desirable trans form.

It is an objective of the present invention to provide a process for the recovery and purification of DHA Triglycerides from fatty oils such as crude fish oils.

SUMMARY

The process of the present invention relates to the purification of DHA (Docosahexaenoic acid) Triglycerides directly from a fish oil feedstock using novel chromatographic techniques. More specifically, Applicant has developed a novel simulated moving bed separation process (SMB) series of adsorbent/desorbent combinations and SMB configurations to bring about the enrichment and purification of DHA (Docosahexaenoic acid) Triglycerides from fish oils directly from the crude fish oils without breaking down the triglycerides into fatty acids and without extreme chemical and physical separation conditions such as molecular distillation or the use of supercritical pressure. The simulated moving bed system employed is a polar phase SMB using a silica based stationary phase adsorbent in combination with a non-polar desorbent to provide an enriched extract stream rich in DHA triglycerides, and a primary raffinate product. The primary raffinate can be evaporated to recover mobile phase desorbent from a residual oil phase which can be used as a biodiesel product. A DHA (Docosahexaenoic acid) Triglyceride product having a purity greater than 97 wt percent (e.g., 98, 99, 99.5 wt-%) following solvent removal can be obtained.

In one embodiment, the invention is a process for the direct extraction of an omega-3 fatty acid enriched triglyceride product comprising an amount of unsaturated triglycerides from a crude fish oil comprising said unsaturated triglycerides and saturated triglycerides having strands comprising fatty acids of at least one of stearic acid, palmitic and oleic acid. The unsaturated triglycerides have at least one fatty acid strand of docosahexaenoic acid (DHA) or eicosapentaenoic acid (EPA). Each triglyceride in the crude fish oil can be characterized by a Partition Number (PN) according to the formula:

$$PN=TC-2DB$$

wherein TC is a total number of carbon atoms in the fatty acid strand, and DB is the number of double bonds in the fatty acid strand. The process comprises:

a. passing the crude fish oil to a solvent mixing zone and therein admixing the crude fish oil with a solvent comprising a non-polar solvent to provide an oil/solvent mixture;

b. passing the oil/solvent mixture to a filtration zone having a filtration media having a filter size less than 0.45 microns to provide a filtered feedstock:

c. passing the filtered feedstock and a mobile phase desorbent to a polar phase simulated moving bed adsorption (SMB) zone, said polar phase SMB zone containing a hydrophilic stationary phase agent comprising silica, the normal phase SMB zone comprising a plurality of adsorbent beds and operating in an effective polar phase cycle, said mobile phase desorbent comprising a non-polar solvent and an organic polar solvent in an effective normal phase solvent ratio of from 95 to 99 parts non-polar solvent such as n-heptane or hexane to 5-1 parts polar organic compound to provide an SMB extract stream, a primary SMB raffinate stream, and a secondary SMB raffinate stream at least a portion of which is recycled to provide at least a portion of the mobile phase desorbent, the SMB extract stream comprising non-polar solvent and an enhanced amount of unsaturated triglycerides relative to the amount of unsaturated triglycerides in the crude fish oil, the unsaturated triglycerides having a PN less than or equal to 36 relative to the and other unsaturated triglycerides of fatty acids, the primary SMB raffinate stream comprising non-polar solvent and unsaturated triglycerides having a PN greater than or equal to 48 and comprising fatty acid strands including palmitic or stearic or oleic acid;

d. passing the SMB extract stream to an extract solvent recovery zone and therein recovering the non-polar solvent to provide the omega-3 fatty acid enriched triglyceride product comprising unsaturated triglycerides having strands comprising EPA or DHA or mixtures thereof and a first recovered solvent stream comprising the non-polar solvent, and passing the primary raffinate stream to a raffinate solvent recovery zone and therein recovering the non-polar solvent to provide an SMB reject stream and a second recovered solvent stream comprising the non-polar solvent and the polar organic solvent;

e. returning at least a portion of the first recovered solvent stream and the second recovered solvent stream to be admixed with the mobile phase desorbent; and, f. withdrawing the omega-3 fatty acid enriched triglyceride product.

BRIEF DESCRIPTION OF THE DRAWINGS

FIG. 5 is a gas chromatographic area plot showing the results of a composition analysis of the raffinate stream withdrawn from the SMB zone of the present invention.

DETAILED DESCRIPTION OF THE INVENTION

Figure 1:
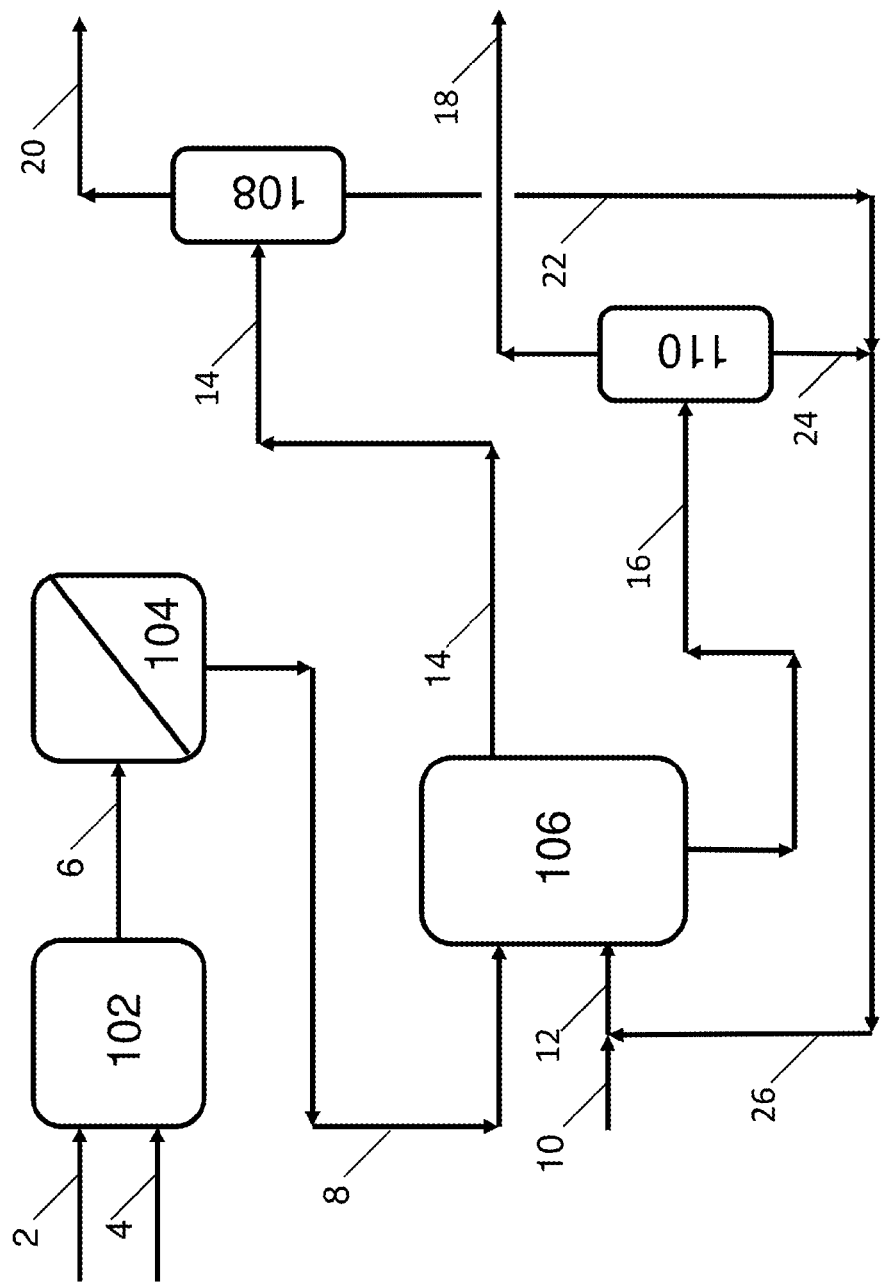
FIG. 1 is a schematic process flow diagram illustrating one embodiment of the invention.

Crude fish oil as described hereinabove comprises triglycerides which have a number of fatty acid components associated with a triglyceride back bone as described hereinbelow. The major fatty acid components are listed in Table 1 and will be referred to by the abbreviation shown in Table 1 for each of the corresponding major component.

TABLE 1

Nomenclature and Abbreviations for Fatty Acids

| Component | Abbreviation | NAME OF COMPONENT |
|---|---|---|
| C16:0 | PAL | PALMITIC ACID (SATURATED)* |
| C18:0 | STA | STEARIC ACID (SATURATED) |
| C18:1 | OLE | OLEIC ACID |
| C18:2 | LIN | LINOLEIC ACID |
| C18:3 | ALA | ALPHA LINOLENIC ACID |

TABLE 1-continued

Nomenclature and Abbreviations for Fatty Acids

| Component | Abbreviation | NAME OF COMPONENT |
|---|---|---|
| C18:4 | SDA | STEARADONIC ACID |
| C20:4 | ETA | EICOSATETRAENOIC ACID |
| C20:5 | EPA | EICOSAPENTAENOIC ACID |
| C22:5 | DPA | DOCOSAPENTANOIC ACID |
| C22:6 | DHA | DOCOSAHEXAENOIC ACID |

The first number in the first column of Table 1, indicates the length of the carbon chain in the fatty acid ester molecule, and the second number indicates the number of double bonds in the molecule. Palmitic acid (PAL) and Stearic acid (STA) are common saturated fatty acids found in animals and plants.

The major source of DHA is from marine oils. Marine micro algae are also a known source of DHA. The DHA content in microalgae is very small. Naturally occurring marine oils form triglycerides with any of 3 fatty acid chain combinations. The chance that 3 DHA fatty acids occur in the same triglyceride is very small. However, DHA is always present along with other fatty acids forming various combinations in the triglyceride. It has been found that the most favorable position for the DHA strand is either the $R^1$ or $R^3$ position in the triglyceride back bone. See typical triglyceride structure hereinbelow showing the relative position in the triglyceride molecule:

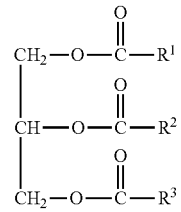

Because of this mixed occurrence, the purification and concentration of the DHA strand alone becomes a challenge. This varied structure of the triglyceride has been the primary reason why the triglycerides are conventionally esterified to unify all the DHA as esters prior to any purification. Because the triglycerides can have any combination of the individual poly unsaturated fatty acid molecule, the relative adsorption and desorption characteristics of each triglyceride in a chromatographic separation will depend upon the particular components attached to the triglyceride back bone. Applicant discovered a method of characterizing the relative separation of triglycerides using a "Partition Number" (PN) as a measure of the chromatographic separation to extract unsaturated triglycerides containing polyunsaturated fatty acids such as EPA and DHA while rejecting saturated triglycerides containing components such as Palmitic (PAL) and Stearic (STA) acid. The separation can be represented using the Partition Number (PN) which is defined as

PN=TC-2DB wherein: TC is the total number of carbon atoms in the triglyceride, and DB is the number of double bonds in the molecule. For example, a triglyceride comprising or containing three Stearic Acid groups has a PN value of 54, and a PN for a triglyceride comprising three EPA components has a PN value of 30. Applicant's process was found to selectively extract unsaturated triglycerides, i.e., having a PN value of less than or equal to about 36 and reject saturated triglycerides, i.e., having a PN value above about 48. For components having a PN value between about 36 and about 48, the distribution of the triglycerides are split between the extract and the raffinate streams. To further illustrate the influence of the triglyceride fatty acid components on the PN value, a determination of the PN is shown for particular combination of the fatty acid components in the triglyceride molecules of various combinations in Table 2.

TABLE 2

Determination of Partition Number in Triglyceride Molecule

| Triglyceride Acid FAC Components* | TC | DB | PN |
|---|---|---|---|
| sss | 54 | 0 | 36 |
| doo | 54 | 3 | 48 |
| lll | 54 | 6 | 48 |
| lnlnln | 54 | 9 | 36 |
| ppp | 48 | 0 | 48 |
| ppo | 50 | 1 | 48 |
| poo | 52 | 2 | 48 |
| pll | 52 | 4 | 44 |
| eee | 60 | 15 | 30 |
| ddd | 66 | 18 | 30 |
| eeo | 58 | 11 | 36 |
| ddo | 62 | 13 | 36 |
| eel | 58 | 12 | 34 |

*wherein the fatty acid components (FAC) are
FAC  Component Name
s  Stearic Acid
o  Oleic
l  Linoleic
ln  Linolenic
p  Palmitic
e  EPA
d  DHA The enrichment of DHA containing triglyceride product obtained by the process of the present invention will dependent upon the initial content of EPA and DHA in the feedstock used as the starting feed material. For example, a crude fish oil derived from tuna oil having triglycerides comprising 30 wt-% EPA and DHA can be enhanced to provide an enhanced triglyceride product comprising about 60 wt-% triglycerides comprising EPA and DHA.

Commercially available triglyceride feedstocks for the present invention ranged from about 25 percent DHA to about 50 percent DHA. Table 3 shows the composition range of typical commercial marine oil feedstock compositions which can be purified by the process of the present invention.

TABLE 3

Feedstock Composition Range for Low and High DHA Content

| Component | Low DHA Feedstock | High DHA Feedstock |
|---|---|---|
| PAL | 18.1 | 2.65 |
| LIN | 1.4 | 2.5 |
| OLE | 12.18 | |
| GLA | | 0.346 |
| ALA | | 0.37 |
| SDA | 1.05 | 0.63 |
| EPA | 6 | 11.3 |
| DPA | 1.3 | 9 |
| DHA | 25 | 50.6 |

Applicant discovered various combinations of a hydrophilic stationary phase agent and polar/non-polar mobile phase desorbent mixture in a polar phase continuous simulated moving bed (SMB) chromatographic separation process to directly purify DHA triglycerides (TAG's) in natural form, without requiring chemical or enzymatic pretreatment, or conversion to esters. Applicant's process was discovered to extract unsaturated triglycerides (having unsaturated fatty acid components such as EPA and DHA) while rejecting saturated triglycerides (having saturated fatty acid components such as Palmitic(PAL) and Stearic acid(STA)).

Stationary Phase

The stationary phase adsorbent for use in the polar phase SMB zone is a hydrophilic adsorbent, such as silica. It was found that silica provided higher selectivities for triglycerides comprising or having a low PN (less than or equal to 40), i.e., triglycerides comprising unsaturated fatty acid components of EPA and DHA than hydrophobic adsorbents such as coated silica adsorbents such as C8 or C18. Batch chromatographic separation showed the ability of the silica adsorbent to perform the enrichment of the EPA and DHA component while significantly rejecting the saturated triglycerides characterized by a higher PN and having saturated fatty acid groups such as Oleic, Linoleic, and Stearic components in the extract stream by using a non-polar solvent as the loading solvent and a polar solvent as the desorbent solvent. Preferably the stationary phase adsorbent is silica having a particle diameter of about 100 microns, 200 microns, and about 300 to about 500 microns with a porosity ranging from about 60 Angstroms to about 120 Angstroms.

Mobile Phase Desorbent

The mobile phase desorbent of the present invention for use in the polar phase SMB zone when the stationary phase is a silica adsorbent is a mixture of a non-polar solvent such as n-heptane or hexane, and a polar organic solvent such as ethyl acetate or acetone. Preferably, the ratio of ethyl acetate or acetone polar solvent is to the non-polar solvent is between 5 to 15 volume percent and the remainder is the non-polar solvent, such as heptane. Applicant discovered that when the ethyl acetate or acetone concentration in the desorbent approached 50 volume percent, the retention on the stationary phase was reduced and the separation efficiency diminished significantly. More preferably, the selective mobile phase desorbent comprises from 95 to 99 parts non-polar solvent such as n-heptane or hexane to 5-1 parts polar organic compound, such as ethyl acetate, and most preferably, the selective mobile phase desorbent comprises a ratio of 98 parts n-heptane or hexane to 2 parts ethyl acetate.

Feed Preparation

In the present invention, the crude fish oil is admixed with a solvent, or the mobile phase desorbent, which is selected for its compatibility with the stationary phase and the operation of the simulated moving bed separation (SMB) process. Preferably, the crude fish oil is admixed with a solvent or solvent mixture to provide a feedstock which comprises from about 2 wt-% to about 10 wt-% crude fish oil in the solvent or solvent mixture. More preferably, the feedstock comprises from about 5 wt-% to about 10 wt-% crude fish oil in a solvent or solvent mixture. Most preferably, the feedstock comprises from about 5 wt-% to about 7 wt-% crude fish oil in a solvent or solvent mixture.

DETAILED DESCRIPTION OF THE DRAWINGS

According to one embodiment of the invention and with reference to FIG. 1, a crude fish oil stream in line 2 is passed to a solvent mixing zone 102, wherein the crude fish oil stream in line 2 is admixed with a non-polar solvent stream in line 4 to provide a fish oil/solvent mixture in line 6. The crude fish oil stream comprises triglycerides having components of fatty acids of omega-3 fatty acids of eicosapentaenoic acid (EPA) or docosahexaenoic acid (DHA), saturated triglycerides having saturated fatty acid components such as palmitic acid(PAL) and stearic acid(STA), along with other unsaturated triglyceride species having saturated fatty acid components including at least one of docosapentanoic acid (DPA), stearadonic acid (SDA), alpha linolenic acid (ALA), gamma linolenic acid (GLA), linoleic acid (LIN) and oleic acid (OLE) and free fatty acids, and depending upon the source also may contain saturated triglycerides having saturated fatty acid components including stearic acid (STA) and palmitic acid (PAL). Preferably, the non-polar solvent is selected from the group consisting paraffinic hydrocarbons such as hexane and heptane. More preferably, the non-polar solvent is heptane. Preferably, the fish oil/solvent mixture comprises a ratio of non-polar solvent to fish oil of from about 2 to about 3 times the volume of the fish oil. More preferably, the fish oil/solvent mixture comprises a ratio of non-polar solvent to fish oil of from about 2.3 to about 2.7 times the volume of the fish oil. Most preferably, the fish oil/solvent mixture comprises a ratio of non-polar solvent to fish oil of from about 2.5 times the volume of the fish oil. The fish oil/solvent mixture in line 6 is passed to a filtration zone 104, wherein the fish oil/solvent mixture is filtered through an ultrafine filter having a filter size less than about 0.45 micron to remove any silt and fine particles from the fish oil/solvent mixture prior to passing the filtered feedstock in line 8 to a simulated moving bed separation zone 106. The filtered feed stock in line 8 and a mobile phase desorbent in lines 10 and 12 are passed to the simulated moving bed separation zone 106. The mobile phase desorbent stream in line 2 comprises a mixture of from 95 to 99 parts n-heptane or hexane to 5-1 parts a polar organic compound, such as ethyl acetate. Most preferably, the first mobile phase desorbent stream comprises a ratio of 98:2 parts n-heptane to ethyl acetate. The simulated moving bed separation zone 106 comprises or contains a plurality of adsorbent beds (at least 8 adsorbent beds) arranged serially in a manner which is described hereinbelow in FIG. 2. Each adsorbent bed contains a stationary phase adsorbent, such as silica. According to the present invention, the stationary phase adsorbent comprises a silica adsorbent and the simulated moving bed separation zone is operated in a polar phase manner, wherein the key product, comprising the polyunsaturated triglyceride components is withdrawn in the extract stream in line 14, and the saturated triglyceride components are withdrawn in the raffinate stream in line 16. The SMB operation of the present invention substantially removes saturated triglycerides having saturated fatty acid components such as OLE and LIN, such saturated triglycerides having a PN greater than or equal to about 40 from the feedstock to provide an extract stream comprising unsaturated triglycerides having a PN less than or equal to about 40 and comprising unsaturated fatty acid components on a solvent free basis), and a raffinate stream comprising unsaturated triglycerides having saturated fatty acid components (on a solvent free basis) and having a PN greater than 40. The extract stream in line 14 is passed to an extract solvent recovery zone 108, wherein a first recovered mobile phase desorbent in line 22 is separated from the extract stream to provide an extract product in line 20. The raffinate stream in line 16 is passed to a raffinate solvent recovery zone, wherein a second recovered mobile phase desorbent stream in line 24 is separated from the raffinate stream in line 16 to provide a raffinate product in line 18. At least a portion of the first recovered mobile phase desorbent stream in line 22 is returned to the SMB zone 106 via lines 22, 26 and 12, and at least a portion of the second recovered mobile phase desorbent stream is returned to the SMB zone 106 via lines 24, 26, and line 12.

The SMB raffinate stream in line 16 comprises the non-polar solvent, and saturated triglycerides having a PN greater than about 40 and saturated fatty acid strands such as OLE(Oleic), LIN(Linoleic), and optionally, palmitic acid. A first secondary SMB raffinate stream, not shown, is also produced and employed directly as first mobile phase desorbent recycle stream of which at least a portion is combined with the mobile phase desorbent stream in line 12 to offset the overall requirement for the mobile phase desorbent stream. The mobile phase desorbent stream in line 10 and/or 12 comprises a mixture of from 95 to 99 parts n-heptane or hexane to 5-1 parts a polar organic compound, such as ethyl acetate. Most preferably, the mobile phase desorbent stream comprises a ratio of 98:2 parts n-heptane to ethyl acetate. The first SMB zone 106 has a plurality of adsorbent beds (at least 8) containing a stationary phase adsorbent and arranged serially in a manner which is described hereinbelow in FIG. 3. The first stationary phase adsorbent is a silica adsorbent. The SMB extract stream in line 14 comprises heptane, ethyl acetate, and triglycerides having unsaturated fatty acid components and other triglycerides having other fatty acid components of at least one of DPA, SDA, ALA, and GLA. If triglycerides comprising unsaturated fatty acid components such as DPA or DHA were present in the filtered feedstock stream in line 8, then triglycerides comprising unsaturated fatty acid components such as DPA and DHA also would be present in the SMB extract stream in line 14. The SMB raffinate stream in line 16 comprises saturated triglycerides having saturated fatty acid components of OLE, LIN, and the polar and non-polar solvents such as heptane and ethyl acetate. The extract concentration of triglycerides having unsaturated fatty acid components such as EPA in the SMB extract stream in line 14 is enhanced relative to the feed concentration of triglycerides having unsaturated fatty acid components such DHA and EPA in the filtered feedstock in line 8. The SMB extract stream in line 14 is passed to an extract solvent recovery zone 108 to separate the triglycerides from the solvents to provide a solvent free extract stream, or an enhanced unsaturated triglyceride product stream, in line 20 comprising the unsaturated fatty acid triglycerides of EPA or DHA or mixtures thereof, and a first recovered solvent stream in line 22, consisting of the non-polar solvent, heptane, and polar solvent, ethyl acetate. The solvent free extract stream is essentially free of non-polar solvent having less than about 30 ppm non-polar solvent. The solvent free extract stream is optionally passed to a further finishing zone (not shown) wherein the first solvent free extract stream is contacted with a silica adsorbent to substantially remove any remaining non-polar solvent from the solvent free extract stream. The raffinate stream in line 16 is passed to a raffinate solvent recovery zone 110 to separate the saturated triglyceride phase comprising non-polar solvent and triglycerides having saturated components including LIN and OLE, from the non-polar solvent to provide an SMB reject stream in line 18 and a second recovered solvent stream in line 24, consisting of the non-polar solvent, heptane and ethyl acetate. The SMB reject stream in line 18 can be employed as a component of biodiesel. The solvent recovery zones 108 and 110 separate the solvent at a pressure lower than atmospheric pressure by wiped film evaporization or vacuum distillation. Typically, the vacuum separation is carried out at an evaporation or vacuum separation temperature of less than or equal to 40° C. at a vacuum pressure of less than or equal to 52 mmHg (27 in Hg or 6.97×10³ pascals). At least a portion of each of the first recovered solvent stream in line 22 and the second recovered solvent stream in line 24 are recycled to makeup a portion of the mobile phase desorbent stream via lines 26 and 12.

Figure 2:
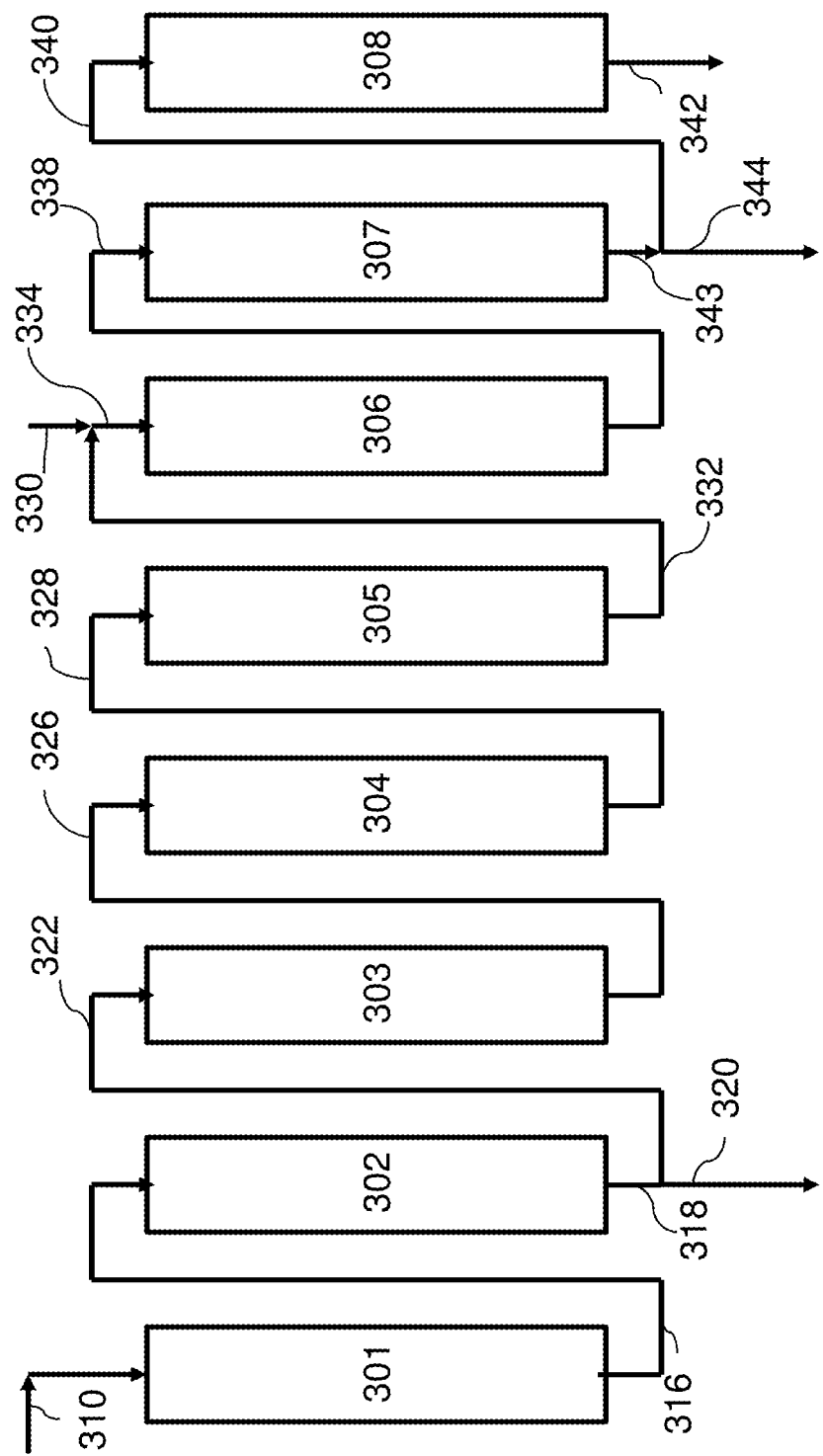
FIG. 2 is a schematic process flow diagram illustrating a configuration of the simulated moving bed cycle in one embodiment of the invention.

Referring to FIG. 2, one embodiment of the simulated moving bed zone of the present invention as used in each of the SMB zones described hereinabove is shown herein as operating in a simulated moving bed (SMB) cycle based on an eight adsorbent bed arrangement. Adsorbent beds 301, 302, 303, 304, 305, 306, 307, and 308, containing a stationary phase adsorbent as described hereinabove, are disposed in a serial configuration such that in accordance with a prearranged cycle, conduit 316 provides fluid communication between the bottom of adsorbent bed 301 with the top of adsorbent bed 302, conduits 318 and 322 provide fluid communication between the bottom of adsorbent bed 302 bed and the top of adsorbent bed 303, conduit 326 provides fluid communication between the bottom of adsorbent bed 303 with the top of adsorbent bed 304, conduit 328 provides fluid communication between the bottom of adsorbent bed 304 with the top of adsorbent bed 305, conduits 332 and 334 provide fluid communication between the bottom of adsorbent bed 305 with the top of adsorbent bed 306, conduit 338 provides fluid communication between the bottom of adsorbent bed 306 with the top of adsorbent bed 307, conduits 343 and 340 provide fluid communication between the bottom of adsorbent bed 307 with the top of adsorbent bed 308, and conduit 344 provides for the withdrawal of fluid from the bottom of adsorbent bed 307 as the primary raffinate, and line 342 provides for the withdrawal of a secondary raffinate or void volume flush of the adsorbent bed 308 which is in transition from the desorption zone to the adsorption zone. At least a portion of the secondary raffinate in line 342 can be used as desorbent and admixed with the desorbent stream in line 310 (not shown) to offset the demand for desorbent in the SMB process. According to the prearranged SMB cycle of the present invention, an SMB zone feed stream is passed to the SMB adsorption zone in line 330 and 334 to adsorbent bed 306. A primary raffinate stream is withdrawn from adsorbent bed 307 in conduits 343 and 344, and an extract stream is withdrawn via conduits 318 and 320 from adsorbent bed 302. A mobile phase desorbent stream as described hereinabove is introduced to adsorbent bed 301 in conduit 310. In this embodiment, the adsorbent beds 301-308 are indexed according to a 2-3-2-1 SMB cycle such that at least 2 adsorbent beds (301 and 302) undergo desorption in a desorption zone, at least 3 adsorbent beds (303, 304, and 305) undergo rectification in a rectification zone, and at least 2 adsorbent beds (306, and 307) undergo adsorption in an adsorption zone, and one bed is idle (308) during the SMB cycle of the present invention.

Applicant discovered an effective SMB cycle for an 8 adsorbent bed SMB unit was a 2-3-2-1, and that effective SMB cycle for a 15 adsorbent bed unit was a 4-4-4-3 cycle.

The following examples are provided to illustrate the present invention. These examples are shown for illustrative purposes, and any invention embodied therein should not be limited thereto.

EXAMPLES

Example 1

Polar Phase SMB with 95:5 Heptane to Ethyl Acetate 50 grams of High DHA feedstock shown in Table 1 was diluted to provide a 10 wt-% feed stream by adding a sufficient amount of a 95:5 volume ratio of heptane:ethyl acetate solution to provide a diluted feed stream. This diluted feed stream was charged to an 8 bed, simulated moving bed system, configured to operate in a 2-3-2-1 cycle (See FIG. 3). Each of the 8 adsorbent beds was 300 mm in length and 22 mm in diameter having a volume of about 114 ml and filled with about 80-85 gm of silica adsorbent having a particle size of 40-63 microns (Available from SiliCycle Inc. China). The SMB columns were preconditioned with a desorbent containing a 95:5 volume ratio of heptane:ethyl acetate to remove any fines which may have been present. It was found that when the desorbent had a 90:10 volume ratio of heptane:ethyl acetate the desorbent was too strong, and when the desorbent had a ratio of 98:2 heptane:ethyl acetate the desorbent was too weak to desorb the adsorbed species. The following flow conditions established in the SMB system are shown in Table 4.

TABLE 4

Polar Phase Flow Conditions of Example 2

| Stream | Flow Rate | Unit |
|---|---|---|
| Feed | 6 | ml/min |
| Desorbent | 36 | ml/min |
| Primary Raffinate | 20 | ml/min |
| Extract | 12 | ml/min |
| Secondary Raffinate | 10.0 | ml/min |

The SMB system was allowed to attain equilibrium and the extract stream and the primary raffinate stream were collected. The mass percent of the material in each of the exit streams was as follows:

| Stream | Mass-% |
|---|---|
| Extract | 70 |
| Primary Raffinate | 30 |
| Secondary Raffinate | 0 |

The secondary raffinate stream was completely recycled (100%) to offset the desorbent stream demand. The extract stream and the primary raffinate stream were collected and the solvent in each stream was evaporated to provide 15 mg of primary raffinate and 35 mg of extract. The extract stream and raffinate stream composition is shown in Table 5 hereinbelow:

TABLE 5

Composition of Extract and Raffinate from High DHA Feed Fish Oil

| Composition | Extract, wt-% | Raffinate, wt-% |
|---|---|---|
| DHA | 68 | 7 |
| EPA | 18 | 26 |
| Unsaturated Triglycerides DPA, SDA | Remainder | |
| Saturated & Unsaturated Triglycerides | | Remainder |

Analytical Methods:

The streams produced were analyzed in the following manner:

Triglyceride Analysis was carried out by HPLC. The HPLC was equipped with Reliasil ODS C18 column (250 mm×4.6 mm, and the C18 adsorbent had a particle size of 3 μm, (Available from Orochem Technologies Inc., IL, USA). The Reliasil column was maintained at 45° C., and eluted with an isocratic solvent system comprising 1:1 Acetone: Acetonitrile at 1.0 ml/min. The detection was made by a Waters 410 Differential Refractometer (Available from Waters-Milford, Mass.). Samples were dried to remove any solvent present and diluted into a 10% solution with Acetone. 20 μl (microliter) injections were made for each sample. The peaks were detected using the RI and the resolved sample components were identified by comparison with peak retention times and calibration curves of standard components.

Ester Analysis was Made by GC Analysis:

Ester samples were analyzed on a HP6890 GC (Available from Hewlett Packard). A DBWax column (Available from Agilent Technologies-Santa Clara, Calif.) was used for separation of the components in each sample. A gradient system was set up for the GC as shown in the Table 6 below.

TABLE 6

GC Gradient System

| Analysis Column | Ester Analysis DBWax | Units |
|---|---|---|
| Dimension | 0.25 × 50 × 0.25 | mm × m × μm |
| | Injection Port | |
| Inlet Temp | 250 | ° C. |
| Injection | Split | |
| Split Ratio | 50-1 | |
| Total Flow | 161 | ml/min |
| | Gradient setting | |
| Oven Temp Rate | Temp | Stay |
| C./min | ° C. | Min |
| | 170 | 2 |
| 3 | 240 | 3 |
| | Detector Port | |
| Detector Temp | 270 | ° C. |
| Hydrogen Flow | 30 | ml/min |
| Air Flow | 400 | ml/min |
| Nitrogen Flow | 30 | ml/min |

Ester sample injections were carried out at 1 μl per sample with a 10 syringe.

HPLC Analysis:

HPLC was equipped with Reliasil C18 column (150 mm×4.6 mm, 5 μm Particle size)(Available from Orochem Technologies Inc., IL, USA). At 25° C., the HPLC column was eluted with isocratic solvent system of 100% methanol at a rate of 1.0 ml/min. The Reliasil C18 column was maintained at 25° C. The detection was made by a Waters 410 Differential Refractometer (Waters-Milford, Mass.). Samples were dried to remove any solvent present and made into a 10% solution with methanol. 20 ul injections were made for each sample. The peaks were detected using the RI and the resolved sample components were identified by comparison with peak retention times and calibration curves of standard components. The following conditions were employed for the HPLC:

| Analysis | Ester Analysis | |
|---|---|---|
| Column | Reliasil C30 | |
| Dimension | 250 × 4.6 | mm × mm |
| Desorbent | 98:2 - Methanol:Water | |
| Flow Rate | 1 | ml/min |
| Temperature | 25 | C. |
| Detection | RI | |

Figure 3:
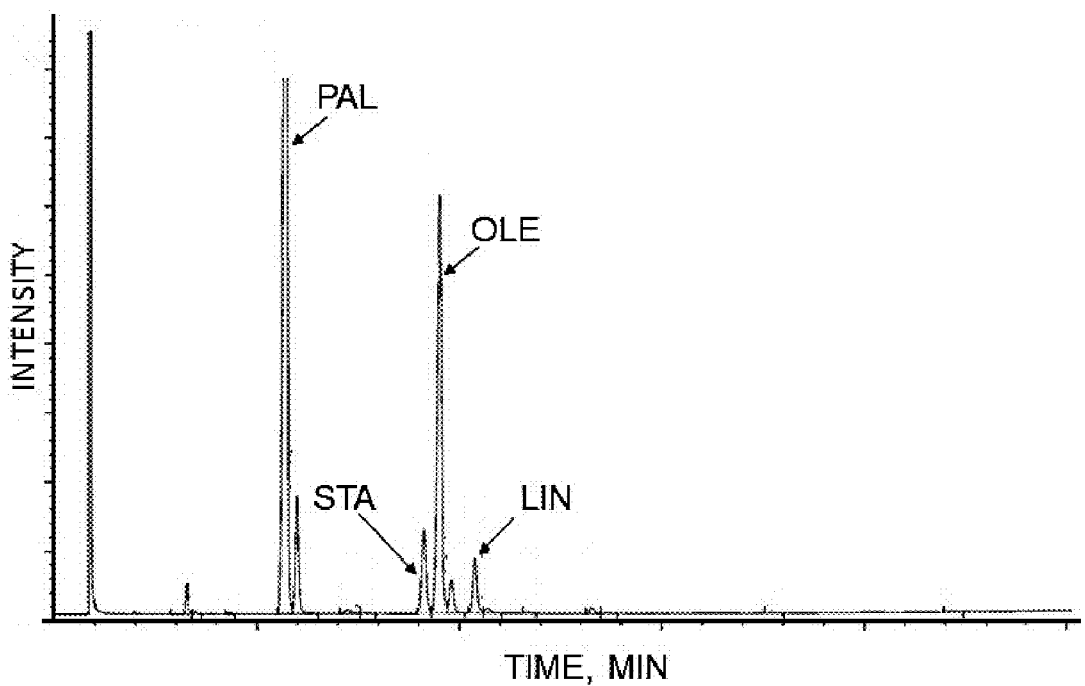
FIG. 3 is a gas chromatographic area plot of the composition of a fish oil ester layer showing the results of a composition analysis of the crude fish oil.
Figure 4:
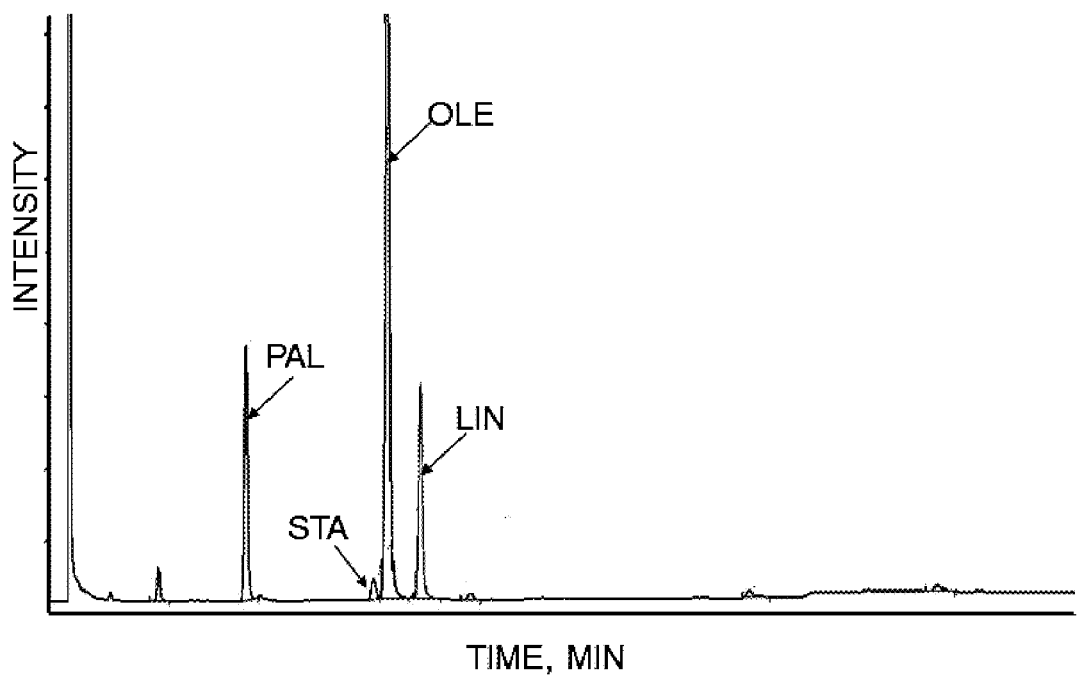
FIG. 4 is a gas chromatographic area plot showing the results of a composition analysis of the extract stream from fish oil withdrawn from the SMB zone of the present invention.

The analytical results for the feedstock, the extract stream and the raffinate stream of Example 1 were depicted in graphical form in the FIG. 3, FIG. 4, and FIG. 5.

FIG. 3 shows the gas chromatographic area plot of the ester layer showing the results of a composition analysis of the fish oil of Example 1 following the hereinabove described analytical methods.

FIG. 4 shows the gas chromatographic area plot showing the results of a composition analysis of the extract stream withdrawn from the SMB zone of Example 1 following the hereinabove described analytical methods.

FIG. 5 shows the gas chromatographic area plot showing the results of a composition analysis of the primary raffinate stream withdrawn from the SMB zone of Example 1, following the hereinabove described analytical methods.

FIG. 4 shows the gas chromatographic analysis of the extract stream of Example 1. FIG. 4 indicates that the recovery of unsaturated omega-3 fatty acids of eicosapentaenoic acid (EPA) or docosahexaenoic acid (DHA) along with other unsaturated triglyceride species including at least one of docosapentanoic acid (DPA,) while rejecting the saturated species of saturated triglycerides such as Palmitic (PAL) (when present) and Stearic acid(STA). Furthermore, the extract stream was essentially free of any OLE or LIN; that is, that there was no detectable concentration of OLE or LIN in the SMB extract. FIG. 5 shows the gas chromatographic analysis of the raffinate stream of Example 1. FIG. 5 clearly shows that the Stearic acid species SDA and STA, along with the linoleic acid species are rejected in the SMB raffinate of Example 1. The DHA Triglyceride purity was 68 mass-% on a solvent free basis and the DHA Triglyceride recovery was 75 mass-% on a solvent free basis.

Example 2

Low DHA Triglyceride Feedstock SMB Triglyceride Separation

The procedure of Example 1 was repeated with a sample of the Low DHA Feed shown in Table 2. Table 7 summarizes the composition of the resulting extract and raffinate stream withdrawn from the 8-bed SMB system on a solvent free basis. The stationary phase was silica and the mobile phase desorbent was 95 parts heptane to 5 parts ethyl acetate. The DHA triglyceride recovery was 31 mass-% on a solvent free basis, and the purity of the DHA triglyceride was 46 mass-% on a solvent free basis, and the extract product has the same polyunsaturated triglyceride structure as the feedstock.

TABLE 7

Composition of Extract and Raffinate from a Low DHA Feedstock

| Component | Feedstock | Extract | Raffinate |
|---|---|---|---|
| PAL | 22.3 | 8.9 | 14 |
| LIN | 13.5 | 1.2 | 2 |
| OLE | 5.0 | 6.0 | 3.0 |
| GLA | 0.86 | | 1.35 |
| ALA | 0.67 | | 0.7 |

TABLE 7-continued

Composition of Extract and Raffinate from a Low DHA Feedstock

| Component | Feedstock | Extract | Raffinate |
|---|---|---|---|
| SDA | 0.3 | 2.0 | 0.6 |
| EPA | 5 | 12 | 4.5 |
| DPA | 2.4 | 4.5 | 5.7 |
| DHA | 22 | 0.7 | 17.8 |

Example 3

Separation of Tuna Oil by PN Value

A tuna oil having a composition comprising about 30 wt-% poly unsaturated fatty acid content as triglycerides was estimated to have the triglyceride profile shown in Table 8. The estimate of the triglyceride structural composition of individual triglycerides in the feed tuna oil were based on the analysis of the extract and raffinate streams, according to the above described analytical method. The tuna oil was subjected to the process of the present invention as described in Example 2. The composition of the feed, extract and raffinate streams is shown in Table 8 in terms of the percentage of triglyceride types (TAG-%) as defined in Table 2, hereinabove. The polyunsaturated fatty acid composition (PUFA) composition clearly shows that the TAG's having a PN less than or equal to 36 were extracted and are shown in the in the extract stream, and the TAGS having a PN greater than or equal to 48 were rejected to the raffinate stream. The extract stream had a composition which comprised 59.6 wt-% triglycerides of poly unsaturated fatty acids such as DHA and EPA. The overall recovery of the PUFA's was about 80 wt-% on a solvent free basis; that is, after evaporization of any solvent from the extract stream.

TABLE 8

Tuna Oil Triglyceride Profile

| TAG | PN | Tuna Oil, TAG-% | Extract, TAG-% | Raffinate, TAG-% |
|---|---|---|---|---|
| sss | 36 | 5 | 0 | 8 |
| ooo | 48 | 7 | 2 | 10 |
| lll | 42 | 5 | 4 | 10 |
| lnlnln | 36 | 5 | 8 | 10 |
| ppp | 48 | 7 | 0 | 12 |
| ppo | 48 | 15 | 10 | 13 |
| poo | 48 | 15 | 10 | 13 |
| pll | 44 | 15 | 10 | 12 |
| eee | 30 | 6 | 10 | 3 |
| ddd | 30 | 4 | 10 | 2 |
| eeo | 36 | 6 | 16 | 3 |
| ddo | 36 | 5 | 10 | 2 |
| eel | 34 | 5 | 10 | 2 |
| PUFA, wt-% | | 29 | 59.6 | 13.7 |

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims, while the description, abstract and drawings are not to be used to limit the scope of the invention. The invention is specifically intended to be as broad as the claims below and their equivalents.

I claim:

1. A process for the direct extraction of an omega-3 fatty acid enriched triglyceride product comprising an amount of unsaturated triglycerides having at least one fatty acid strand of docosahexaenoic acid (DHA) or eicosapentaenoic acid (EPA) from a crude fish oil comprising said unsaturated triglycerides and saturated triglycerides having strands comprising fatty acids of at least one of stearic acid, palmitic and oleic acid, wherein each triglyceride in the crude fish oil can be characterized by a Partition Number (PN) according to the formula:

$$PN=TC-2DB$$

wherein TC is a total number of carbon atoms in the fatty acid strand, and DB is the number of double bonds in the fatty acid strand, said process comprising:
 a. passing the crude fish oil to a solvent mixing zone and therein admixing the crude fish oil with a solvent comprising a non-polar solvent to provide an oil/solvent mixture;
 b. passing the oil/solvent mixture to a filtration zone having a filtration media having a filter size less than 0.45 microns to provide a filtered feedstock:
 c. passing the filtered feedstock and a mobile phase desorbent to a polar phase simulated moving bed adsorption (SMB) zone, said polar phase SMB zone containing a hydrophilic stationary phase agent comprising silica, said polar phase SMB zone comprising a plurality of adsorbent beds and operating in an effective polar phase cycle, said mobile phase desorbent comprising a non-polar solvent and an organic polar solvent in an effective normal phase solvent ratio of from 95 to 99 parts non-polar solvent comprising n-heptane or hexane to 5-1 parts polar organic compound to provide an SMB extract stream, a primary SMB raffinate stream, and a secondary SMB raffinate stream at least a portion of which is recycled to provide at least a portion of the mobile phase desorbent, said SMB extract stream comprising non-polar solvent and an enhanced amount of unsaturated triglycerides relative to the amount of unsaturated triglycerides in the crude fish oil, said unsaturated triglycerides having a PN less than or equal to 36 relative to the and other unsaturated triglycerides of fatty acids, said primary SMB raffinate stream comprising non-polar solvent and unsaturated triglycerides having a PN greater than or equal to 48 and comprising fatty acid strands including palmitic or stearic or oleic acid;
 d. passing the SMB extract stream to an extract solvent recovery zone and therein recovering the non-polar solvent to provide the omega-3 fatty acid enriched triglyceride product comprising unsaturated triglycerides having strands comprising EPA or DHA or mixtures thereof and a first recovered solvent stream comprising the non-polar solvent, and passing the primary raffinate stream to a raffinate solvent recovery zone and therein recovering the non-polar solvent to provide an SMB reject stream and a second recovered solvent stream comprising the non-polar solvent and the polar organic solvent;
 e. returning at least a portion of the first recovered solvent stream and the second recovered solvent stream to be admixed with the mobile phase desorbent; and,
 f. withdrawing the omega-3 fatty acid enriched triglyceride product.

2. The process of claim 1, wherein the wherein the fish oil/solvent mixture has a ratio of 2 to 3 parts non-polar solvent to 1 part crude fish oil.

3. The process of claim 1, wherein the non-polar solvent is hexane or heptane.

4. The process of claim 1, further comprising withdrawing the SMB reject stream for use in biodiesel.

5. The process of claim 1, wherein the mobile phase desorbent is a mixture of the non-polar solvent consisting of heptane or hexane and the organic polar solvent consists of ethyl acetate and the effective normal phase solvent ratio is from about 98 to 99 parts non-polar solvent to 2 to 1 parts polar organic solvent.

6. The process of claim 1, wherein the mobile phase desorbent is a mixture of heptane or hexane and ethyl acetate or acetone and the effective normal phase solvent ratio is 95 parts heptane or hexane to 5 parts ethyl acetate.

7. The process of claim 1, wherein the SMB zone comprises at least eight adsorbent beds and the effective normal phase cycle comprises a 2-3-2-1 SMB cycle such that at least 2 adsorbent beds undergo desorption in a desorption zone, at least 3 adsorbent beds undergo rectification in a rectification zone, at least 2 adsorbent beds undergo adsorption in an adsorption zone, and at least one bed is idle.

8. The process of claim 1, wherein the SMB zone comprises at least eight adsorbent beds containing silica as the hydrophilic stationary phase agent.

9. The process of claim 1, further comprising passing the enhanced triglyceride product stream to a finishing zone to substantially remove any remaining non-polar solvent from the enhanced triglyceride product stream, wherein the finishing zone comprises a silica adsorbent.

10. The process of claim 1, wherein the SMB zone comprises at least 15 adsorbent beds and the effective normal phase cycle comprises a 4-4-4-3 SMB cycle such that at least 4 adsorbent beds undergo desorption in a desorption zone, at least 4 adsorbent beds undergo rectification in a rectification zone, at least 4 adsorbent beds undergo adsorption in an adsorption zone, and at least 3 beds are idle.

* * * * *